United States Patent

Maul et al.

[11] 4,061,688
[45] Dec. 6, 1977

[54] LIQUID PHASE FLUORINATION PROCESS

[75] Inventors: James J. Maul, Grand Island; Victor A. Pattison, Clarence Center, both of N.Y.

[73] Assignee: Hooker Chemicals & Plastics Corporation, Niagara Falls, N.Y.

[21] Appl. No.: 748,018

[22] Filed: Dec. 6, 1976

[51] Int. Cl.$^2$ ............................................. C07C 25/14
[52] U.S. Cl. ............................... 260/651 F; 260/653.8
[58] Field of Search .......................... 260/651 F, 653.8

[56] References Cited

U.S. PATENT DOCUMENTS

| | | | |
|---|---|---|---|
| 3,136,822 | 6/1964 | Frainier | 260/651 F |
| 3,859,372 | 1/1975 | Robota | 260/651 F |
| 3,950,445 | 4/1976 | Ryf | 260/651 F |

*Primary Examiner*—C. Davis
*Attorney, Agent, or Firm*—P. F. Casella; W. J. Crossetta; A. S. Cookfair

[57] ABSTRACT

A process for the preparation of compounds of the formula $$R_nAr(CF_{w'}X_{p'})_Z$$

comprises contacting compounds of the formula $$R_nAr(CF_wX_p)_Z$$

in the liquid phase, with hydrogen fluoride in the presence of fluosulfonic acid wherein Ar is aryl
R is a substituent on the aryl nucleus selected from the group consisting of aryl, substituted aryl, halogen, alkyl, alkoxy, and substituted alkyl;
n is 0 to 9;
X is halogen atom other than fluorine;
w is 0 to 2;
p is 1 to 3;
w' is 1 to 3, and is greater than w;
p' is 0 to 2, and is less than p;
w + p is 3;
w' + p' is 3;
Z is 1–10; and
the maximum value of n + Z is 10.

30 Claims, No Drawings

LIQUID PHASE FLUORINATION PROCESS

BACKGROUND OF THE INVENTION

This invention relates to a process for the preparation of organic fluoride compounds, and in particular, to a process for the liquid phase replacement of halogen atoms with fluorine in organic compounds.

A variety of fluorination processes are known wherein fluorine replaces substituents of organic compounds, such as halogn atoms, and the like. Such known processes include both vapor phase fluorination reactions and liquid phase fluorination reactions. Typically, such processes involve the reaction of an organic halide with hydrogen fluoride, sometimes in the presence of catalyst, such as antimony pentafluoride, at atmospheric or super-atmospheric pressures. Many of the known processes, while suitable for laboratory investigations and experiments, are unsuitable for commercial use for various reasons, such as the low purity of product obtained, the high cost of equipment or catalyst which must be employed, or the need for frequent replacement of the catalyst, due to loss or deactivation. One of the common difficulties encountered in vapor phase fluorination reactions results from the highly exothermic nature of such reactions. The heat evolved frequently results in a temperature rise sufficient to cause thermal decomposition of some of the organic substrates and a resultant carbonization of the catalyst. Furthermore, continuous vapor phase processes are often unsuitable for the preparation of product quantities other than high volume since starting the process usually requires precise control and adjustment of conditions which can result in the waste of reactant materials until ideal reaction conditions are achieved.

Some of the problems associated with vapor phase fluorination processes may be avoided through the use of liquid phase fluorination. However, although atmospheric liquid phase processes are known and are used in laboratory preparations, such processes present various difficulties in larger scale commercial applications. For example, it is known that benzotrifluoride can be prepared by the addition of benzotrichloride to liquid anhydrous hydrogen fluoride at atmospheric pressure with the temperature maintained at between about $-4°$ and $19°$ Celsius. One significant problem with this process is that the reaction rate is relatively slow and therefore the reaction time is in the order of several hours and is undesirably slow for commercial production. Various other liquid phase fluorination processes are known wherein hydrogen fluoride in either gaseous or liquid form is added to a liquid reactant in the presence of a catalyst. Heretofore, the most widely used catalyst for liquid phase fluorination has been antimony pentahalide or a mixture of antimony pentahalide and antimony trihalide. However, antimony halides, and in particular antimony fluorides, although highly effective in the catalysis of fluorination reactions, are relatively expensive materials. To avoid the problems associated with the volatility of hydrogen fluoride, such fluorination reactions are often carried out in closed systems under superatmospheric pressure, necessitating the use of pressure equipment. Thus, although antimony halides provide an effective catalyst for fluorination reactions, a need exists for an effective liquid phase fluorination process that will overcome the aforementioned disadvantages.

It is an object of the present invention to provide an improved process for the liquid phase fluorination of organic halides. It is a further object to provide an improved liquid phase fluorination process wherein the halogen (other than fluorine) on a haloalkyl aromatic compound may be replaced with fluorine under moderate reaction temperatures and at a relatively rapid rate of reaction. It is a still further object to provide an improved liquid phase process for the production of fluoroalkyl aromatic compounds.

SUMMARY OF THE INVENTION

In accordance with the present invention, there is provided a process for the preparation of fluorinated aromatic compounds which comprises reacting a haloalkyl aromatic compound, wherein the halo- is other than fluorine, with a fluorinating agent in the presence of fluosulfonic acid The halomethyl aromatic compound may also contain stable ring constituents, such as halogen, alkyl, alkoxy, substituted alkyl and the like, or other substituents that will not adversely affect the reaction.

In particular, this invention is directed to a process for the preparation of compounds of the formula

which comprises contacting compounds of the formula

in the liquid phase, with hydrogen fluoride in the presence of fluosulfonic acid wherein $Ar$ is aryl;
$R$ is a substituent on the aryl nucleus selected from the group consisting of aryl, substituted aryl, halogen, alkyl, alkoxy and substituted alkyl;
$n$ is 0 to 9;
$X$ is halogen atom other than fluorine;
$w$ is 0 to 2;
$p$ is 1 to 3;
$w'$ is 1 to 3, and is greater than $w$;
$p'$ is 0 to 2, and is less than $p$;
$w + p$ is 3;
$w' + p'$ is 3;
$Z$ is 1–10; and
the maximum value of $n + Z$ is 10.

Among the R substituents encompassed within the formula shown above, are radicals of from 1 to about 20 carbon atoms, and preferably of from 1 to about 12 carbon atoms, such as methyl, ethyl, propyl, butyl, amyl, octyl, decyl, dodecyl, pentadecyl, eicosyl, as well as their various isomer forms, such as isopropyl and isobutyl, said alkyl radical being a monovalent radical derivable from an aliphatic hydrocarbon alkane by the removal of 1 hydrogen atoms; substituted alkyl of from 1 to about 30 carbon atoms and preferably of from 1 to about 15 carbon atoms, said alkyl group being substituted by one or more of aryl, substituted aryl, and the like; alkoxy and substituted alkoxy of from 1 to about 20 carbon atoms, and preferably of from 1 to about 12 carbon atoms, such as methoxy, ethoxy, propoxy, butoxy, pentoxy, octoxy, dodecoxy, pentadecoxy, eicosoxy, as well as their various isomer forms, such as iso-propoxy, iso-butoxy, and the like; and, halogen such as chlorine or bromine. Various other R substituents may be present on the haloalkyl aromatic compound reactants and corresponding products will be obtained. The number ($n$) of R substituents present on the aromatic nucleus is from 0 to 9 and preferably from 0 to 5. The number (Z) of haloalkyl substituents on the aromatic nucleus is from 1 to 10 preferably 1 or 2. The maximum number of substituents (n + Z) is equal to the total number of positions available on the aromatic nucleus. Thus when Ar is benzene, the maximum value of n + Z is 6, and in this instance if the value of n is 3, the maximum value of Z will be 3. Similarly when Ar is naphthalene, the maximum value of n + Z is 8 and when Ar is anthracene the maximum value of n + Z is 10. The preferred compounds which may be fluorinated in accordance with this invention are those of the above formula wherein Ar is benzene, R is chlorine, n is 0 to 2, and Z is 1.

The designation Ar or aryl represent an aromatic structure such as benzene, naphthalene, anthracene and the like, preferably of up to 14 carbon atoms. The preferred compounds prepared in accordance with this invention are those of the above formula wherein Ar is benzene, n is 0 to 5, Z is 1 to 6 and the maximum value of n + Z is 6.

Without being limited to theory, the use of the catalytic acid system, which comprises $HSO_3F$, has several advantages over the prior art methods of liquid phase fluorination. First, it acts as a catalyst by accelerating the reaction between the haloalkyl aromatic substrate and HF. Second, it acts as a solvent for the HF and thereby reduces the vapor pressure of HF in the reaction mixture. Therefore, volatile HF is less likely to be entrained out of the reaction by evolving HCl. In addition, it reduces the required reaction volume since far greater excess of HF would be required to approach the reaction rates if no $HSO_3F$ were present.

The catalytic acid system may advantageously comprise $HSO_3F$ in combination with one or more other components, such as metal halides, which will enhance the acidity of the system. Components which may be advantageously combined with $HSO_3F$ in this manner include, for example $AsF_5$, $SbF_5$, $SbF_5$—$SO_3$ systems and the like.

Since the $HSO_3F$ catalytic acid system may function additionally as a solvent for the hydrogen fluoride reactant, the amount of catalytic acid system employed may vary considerably. Preferably the amount of $HSO_3F$ will be about 25 parts to about 250 parts per 100 parts by weight of the halomethyl aromatic reactant. When one or more additional components such as the aforementioned metal halides are employed in combination with the $HSO_3F$, the amount or proportion of such additional component may vary considerably, but is preferably in a minor proportion such as about 10 to about 75 parts per 100 parts by weight of $HSO_3F$.

In a preferred embodiment, the process of this invention is directed to the fluorination of compounds of the formula

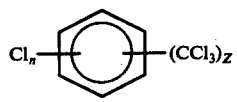

wherein n is 0 to 2 and Z is 1 or 2, and most preferably benzotrichloride, monochlorobenzotrichloride, dichlorobenzotrichloride, and hexachloroxylene, in the presence of a catalytic acid system as described herein. The fluorination occurs on the halomethyl side chain of the aromatic compound with the replacement of the halogen atoms thereof by fluorine. The degree of fluorination will depend in part on the amount of fluorinating agent supplied to the reaction and the length of time the reaction is carried out. Thus, for example, depending on these and other conditions of reactions described hereinbelow, the compound

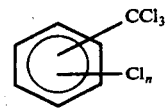

in the liquid phase, may be reacted with hydrogen fluoride, in the presence of fluosulfonic acid to prepare

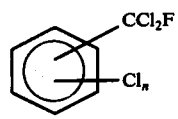 I

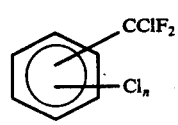 II

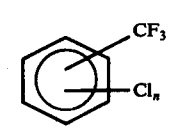 III or mixtures thereof, the composition of which will depend on the amount of hydrogen fluoride reactant. Alternatively, partially fluorinated compounds, such as compounds I and II may be employed as starting materials and further fluorinated by the process of this invention to produce higher fluorinated compounds such as compounds II and III.

The order of addition of reactants may vary. Thus, for example, the halomethyl aromatic compound may be added to a pre-mixed solution of HF and the $HSO_3F$ catalyst acid system, or alternatively, the HF may be added to a liquid either as a liquid or gas mixture of the halomethyl aromatic compound and the $HSO_3F$ catalyst acid system.

In a preferred embodiment, the process of this invention may be carried out by adding the precooled halomethyl aromatic substrate to a solution of HF and $HSO_3F$. The reaction may be stirred or otherwise agitated to ensure adequate contact of the reactants. Additional HF may be added as needed. Furthermore it is an important advantage that when the liquid reaction mixture, comprising HF and the aromatic reactant is allowed to settle, a phase separation occurs with HF (together with the acid catalyst system) forming one phase and the fluorinated aromatic forming a second phase. Additional HF may be added to facilitate the separation. The fluorinated aromatic may then be removed by simple physical separation means, such as decantation, use of a separatory funnel and the like.

In another preferred embodiment of the invention, the precooled halomethyl aromatic is added to the $HSO_3F$ and HF mixture which is preferably stirred or agitated as described above. When the reaction has run to completion (i.e. when HCl evolution ceases), additional HF is added in sufficient amounts to fluorinate another batch of the halomethyl aromatic. Addition of HF functions to extract the $HSO_3F$ from fluorinated aromatic by causing the reactants to form a two phase solution. The fluorinated aromatic phase can then be removed by any means which are well known in the art. Upon removal of the fluorinated aromatic, the HSO₃F and HF solution can be used to fluorinate another batch of halomethyl aromatic. By proceeding in this manner, the efficiency of the overall process may be improved because there may still be some halomethyl aromatic left in the HSO₃F and HF solution upon the removal of the fluorinated aromatic. By using the same HSO₃F and HF solution to fluorinate another batch of halomethyl aromatic, the unreacted aromatic in the acid from the previous batch may then be fluorinated and isolated as useful product.

The amount of catalyst acid system, and ratio of reactants will vary, depending on the nature of the reactants employed, as well as on the products desired. The process may be run in either a batch or continuous manner. Generally, the amount of catalyst acid system to be used is a function of the desired production rate and retention time of the process. Although retention time may vary considerably, it will typically range between about 5 minutes and about 2 hours. Typical conversions obtained have been as high as 98 percent and yields have been greater than 90 percent.

The ratio of hydrogen fluoride to halomethyl aromatic compound reactant may vary considerably, depending on the product desired. The complete fluorination of a trihalomethyl side chain of one mole of an aromatic compound will require at least the theoretical amount of three moles of hydrogen fluoride. Normally, an excess of that stoichiometric amount will be employed since, in practice, the HCl which evolves as the fluorination reaction proceeds, tends to entrain some of the unreacted HF, so that additional amounts of HF, above the theoretical amount, are generally needed. The actual amount of HF required will depend on the efficiency of the condenser. Typically, stoichiometric excess of about 1 to about 2 moles of HF per mole of trihalomethyl is employed when complete fluorine replacement is desired. When partial fluorination is to be effected, proportionally less HF will be employed.

The temperature at which the reaction is effected will depend upon the characteristics of the reactants, such as the volatility, reactivity, and stability, and will normally be in the range of −75° to about 35° Celsius. It is preferred, however, to effect the reaction at a temperature of below about the boiling point of hydrogen fluoride (about 20° Celsius) and most preferably at about −10° to about 10° Celsius. The use of temperatures below about the boiling point of HF will facilitate the retention of that reactant in dissolved form in the fluosulfonic acid. Atmospheric pressure is suitable for operation of the process. However, super- or sub- atmospheric pressures may be employed.

Although it is preferred not to employ in inert solvent for the reaction, one may be utilized if desired to facilitate the reaction. Examples of such solvents include aromatic hydrocarbon solvents such as benzene, and perfluorinated solvents such as perfluorinated alkanes and the like.

The products of this invention are useful for a variety of purposes and are particularly valuable for use as chemical intermediates and dye intermediates, but may also be useful as solvents, herbicides, pesticides, pharmaceuticals and the like.

The following examples will serve to further illustrate the invention and the manner is which it may be practiced. The examples are set forth for purposes of illustration and are not to be construed as limitative of the present invention. Many variations of the process may be made without departing from the spirit and scope of the invention. In the examples, unless otherwise stated, all parts and percentages are by weight and all temperatures are in degrees Celsius.

EXAMPLES 1-4

Examples 1-4 illustrate the dramatic increase in rate of fluorination achieved in accordance with this invention when a portion of the hydrogen fluoride is replaced by fluosulfonic acid. The general procedure employed was as follows: The hydrogen fluoride reactant was cooled to 0° C. (In Examples 2 and 4 a portion of the HF was replaced by an equal volume of HSO₃F). Precooled halomethyl aromatic reactant was added in the proportions shown and the reaction mixture was stirred for the time period shown. At the end of this time period an additional 90 parts of HF was added and the reaction mixture was allowed to settle, forming two phases — a phase or layer of fluorinated aromatic product and a phase of HF. In Examples 2 and 4, the HF layer comprises a solution containing the HSO₃F and some unreacted chlorinated aromatic. The fluorinated aromatic product was decanted into water, washed with 5% sodium bicarbonate, and then analyzed by gas chromatographic techniques.

EXAMPLES 1-4
ILLUSTRATION OF RATE INCREASE WHEN A PORTION OF HF IS REPLACED WITH HSO₃F

| EXAMPLE # | STARTING MATERIAL | MOLE STARTING MATERIAL | HSO₃F | HF | REACTION TIME | AREA % PRODUCTS (GLC) | | | | PRODUCT WEIGHT |
|---|---|---|---|---|---|---|---|---|---|---|
| | | | | | | —CCl₃ | —CCl₂F | —CClF₂ | —CF₃ | |
| 1 | 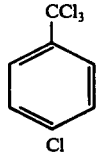 | 1 | — | 165 ml (8.25 moles) | 4 hrs. | 24.6 | 50.3 | 24.4 | 0.4 | 203 g |
| 2 | 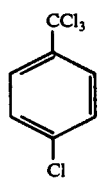 | 1 | 75 ml (1.3 moles) | 90 ml (4.5 moles) | 3.5 hrs. | — | — | 2.4 | 97.6 | 129.6 g |

EXAMPLES 1-4-continued

ILLUSTRATION OF RATE INCREASE WHEN A PORTION OF HF IS REPLACED WITH HSO₃F

| EXAMPLE # | STARTING MATERIAL | MOLE STARTING MATERIAL | HSO₃F | HF | REACTION TIME | AREA % PRODUCTS (GLC) —CCl₃ | —CCl₂F | —CClF₂ | —CF₃ | PRODUCT WEIGHT |
|---|---|---|---|---|---|---|---|---|---|---|
| 3 | 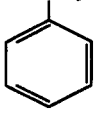 | 1 | — | 165 ml (8.25 moles) | 2.5 hrs. | 1.6 | 20.7 | 70.2 | 7.4 | 154 g |
| 4 | 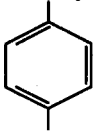 | 1 | 75 ml (1.3 moles) | 90 ml (4.5 moles) | 1.25 hrs. | — | — | — | 100 % | 84 g |

EXAMPLES 5-6

The dramatic acceleration of rate of fluorination when a portion of the HF reagent is replaced by strong acid mixtures is also illustrated in Example 5 and 6. The general procedure of Examples 1-4 was replated, except that the reactant composition was varied as noted.

In Example 5, 0.5 mole of parahexachloroxylene was combined with 165 ml of HF. The reaction was stirred for 5 hours. Essentially no reaction occurred, as evidenced by a complete lack of evolution HCL by-product.

In Example 6, 75 ml (of the 165 ml of HF) was replaced with 75 ml of a solution of SbF₅ in HSO₃F (molar ration SbF₅:HSO₃F = 1:4.2). After stirring for 2.5 hours, the reaction was worked up in the usual manner to yield 77g (71% yield) of hexafluoroxylene.

Example 7 was run as follows:

Cycle 1 — Benzotrichloride (1.0 Mole) was added to a solution of 75 ml of HSO₃F in 90 ml of HF (4.5 mole) at 2° C. After mechanical stirring for about 75 minutes, an additional 4.5 mole of HF (to facilitate separation the fluorinated aromatic product as well as for reaction in the next cycle) was added and the upper, organic liquid was poured into H₂O, washed with 5% aqueous NaHCO₃, dried and analyzed via gas chromatography.

Cycles 2 through 7 — in each cycle benzotrichloride (1 mole) was added to the acid mixture from the previous cycle (10 ml of additional HSO₃F was added before cycle 6) and after mechanical agitation for 60 to 75 minutes an additional 4.5 moles of HF (5 moles after cycle 6) was added to the reaction mixture. After each cycle the upper organic layer was drawn off, poured into water, washed with 5% aqueous NaHCO₃, dried and analyzed by gas chromatography.

EXAMPLES 5-6

Illustration of rate increase when a portion of HF is replaced with a mixed acid catalyst.

| EXAMPLE # | STARTING MATERIAL | MOLES STARTING MATERIAL | ML ACID CATALYST | HF | REACTION TIME | RESULTS |
|---|---|---|---|---|---|---|
| 5 | p-bis(CCl₃)benzene | 0.5 | — | 165 ml (8.25 mole) | 5 hrs. | Essentially no reaction only starting material recovered |
| 6 | p-bis(CCl₃)benzene | 0.5 | 75 HSO₃F:SbF₅ 4.2:1 | 90 ml (4.5 mole) | 2.5 hrs. | p-bis(CF₃)benzene 99% Purity 71% Yield |

EXAMPLE 7

By recycle of the acid catalyst yields of fluorinated product approaching quantitative can be realized.

EXAMPLE 7

| | CYCLE PRODUCTION OF BENZOTRIFLUORIDE INPUT | | | ORGANIC OUTPUT | |
|---|---|---|---|---|---|
| | Moles of benzotrichloride | HF | HSO₃F | Moles of benzotrifluoride | Purity |
| Cycle 1 | 1 mole | 4.5 mole | 75 ml | .58 | 100 |

EXAMPLE 7-continued

| | CYCLE PRODUCTION OF BENZOTRIFLUORIDE | | | | |
|---|---|---|---|---|---|
| | INPUT | | | ORGANIC OUTPUT | |
| | Moles of benzotrichloride | HF | $HSO_3F$ | Moles of benzotrifluoride | Purity |
| | | | (1.34 mole) | | |
| Cycle 2 | 1 mole | 4.5 mole | | .67 | 99.3 |
| Cycle 3 | 1 mole | 4.5 mole | | .77 | 99.5 |
| Cycle 4 | 1 mole | 4.5 mole | | .71 | 99.8 |
| Cycle 5 | 1 mole | 4.5 mole | | .43 | 99.6 |
| Cycle 6 | 1 mole | 4.5 mole | +10 ml (0.17 mole) | 2.0 | 99.7 |
| Cycle 7 | 1 mole | 5.0 mole | | 1.9 | 99.0+ |
| TOTAL | 7 moles | 32 moles | 85 ml (1.41 mole) | 6.35 | >99% |
| Overall Yield % | | | | 90.7% | |
| Yield Runs 2-7 | | | | 96.2% | |

EXAMPLE 8

The following example illustrates an alternate method of this invention wherein the halomethyl aromatic reactant to be fluorinated is dissolved in $HSO_3F$ and then HF bubbled into the solution.

Benzotrichloride (0.5 mole) (precooled to 0° to −2° C.) was added under nitrogen to 25 ml of similarly precooled $HSO_3F$. During 1 hour, gaseous hydrogen fluoride (2 moles) was bubbled into the stirred reaction mixture. The reaction mixture was poured over ice and the organic material was washed successively with water, 5% aqueous potassium bicarbonate and $H_2O$. After drying over magnesium sulfate, the liquid (50.5g.) was shown by gas liquid chromatography to be 99% benzotrifluoride.

What is claimed is:

1. A process for the preparation of fluorinated aromatic compounds of the formula

$$R_nAR(CF_{w'}X_{p'})_Z$$

comprises contacting at least one haloalkyl aromatic compound of the formula

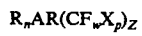
$$R_nAR(CF_wX_p)_Z$$

in the liquid phase, with hydrogen fluoride in the presence of a catalyst acid system comprising fluosulfonic acid wherein
  Ar is aryl
  R is a substituent on the aryl nucleus selected from the group consisting of aryl, substituted aryl, halogen, alkyl, alkoxy, and substituted alkyl;
  n is 0 to 9;
  X is halogen atom other than fluorine;
  w is 0 to 2;
  p is 1 to 3;
  w' is 1 to 3, and is greater than w;
  p' is 0 to 2, and is less than p;
  w + p is 3;
  w' + p' is 3;
  Z is 1-10; and
  the maximum value of n + Z is 10.

2. A process according to claim 1 wherein Ar is benzene, n is 0 to 5, Z is 1-6, and the maximum value of n + Z is 6.

3. A process according to claim 2 wherein R is chlorine, and n is 0 to 2.

4. A process according to claim 3 wherein X is chlorine.

5. A process according to claim 4 wherein Z is 1.

6. A process according to claim 5 wherein p is 3 and w is 0.

7. A process according to claim 6 wherein n is 0.

8. A process according to claim 7 wherein p' is 0 and w' is 3.

9. A process according to claim 6 wherein n is 1.

10. A process according to claim 9 wherein p' is 0 and w' is 3.

11. A process according to claim 2 wherein the haloalkyl aromatic compound is added to a solution of HF and $HSO_3F$ and the resultant reaction mixture is maintained at a temperature of about −75° to about 35° Celsius.

12. A process according to claim 11 wherein the haloalkyl aromatic compound is characterized by the formula

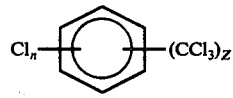

wherein n is 0 to 2 and Z is 1 or 2.

13. A process according to claim 12 wherein n is 0.
14. A process according to claim 13 wherein Z is 1.
15. A process according to claim 14 wherein Z is 2.
16. A process according to claim 15 wherein said haloalkyl aromatic compound is characterized by the formula

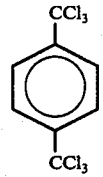

17. A process according to claim 12 wherein n is 1.
18. A process according to claim 17 wherein Z is 1.
19. A process according to claim 18 wherein said haloalkyl aromatic compound is characterized by the formula

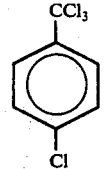

20. A process according to claim 11 wherein the fluorinated aromatic compound prepared is separated from the reaction mixture by the addition of an excess of HF to form a first liquid phase comprising HF and HSO₃F and an second organic liquid phase comprising the fluorinated aromatic compound product and removing the organic phase by physical means.

21. A process according to claim 20 wherein the haloalkyl aromatic compound is characterized by the formula

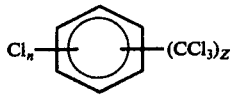

and the fluorinated aromatic product is characterized by the formula

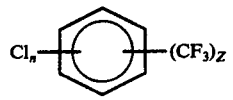

wherein $n$ is 0 to 2 and Z is 1 or 2.

22. A process according to claim 21 wherein $n$ is 0 and Z is 1.

23. A process according to claim 21 wherein $n$ is 1 and Z is 2.

24. A process according to claim 21 wherein $n$ is 1 and Z is 1.

25. A process according to claim 21 wherein the reaction mixture is maintained at a temperature of about $-75°$ to about 20° Celsius.

26. A process according to claim 1 wherein the catalyst acid system comprises fluosulfonic acid and a metal halide which will increase the acidity of the system.

27. A process according to claim 26 wherein the metal halide is SbF₅.

28. A process according to claim 1 which comprises contacting said haloalkyl aromatic compound with a solution comprising hydrogen fluoride and fluosulfonic acid to form a reaction mixture, maintaining the reaction mixture at a temperature of about $-75°$ to about 20° Celsius and periodically adding additional hydrogen fluoride to the reaction mixture to extract fluosulfonic acid therefrom and cause a phase separation into a hydrogen fluoride-fluosulfonic acid phase and a fluorinated aromatic product phase, separating the fluorinated aromatic phase therefrom and adding additional haloalkyl aromatic compound to the remaining reaction mixture.

29. A process according to claim 28 wherein the haloalkyl aromatic compound is benzotrichloride and the fluorinated aromatic compound is benzotrifluoride.

30. A process according to claim 28 wherein the reaction mixture is maintained at about $-10°$ to about 10° Celsius.

* * * * *